(12) United States Patent
Tsuji et al.

(10) Patent No.: US 7,319,177 B2
(45) Date of Patent: Jan. 15, 2008

(54) PROCESS FOR PRODUCING CUMENE

(75) Inventors: Junpei Tsuji, Ichihara (JP); Masaru Ishino, Sodegaura (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 10/540,029

(22) PCT Filed: Dec. 16, 2003

(86) PCT No.: PCT/JP03/16074

§ 371 (c)(1),
(2), (4) Date: Jun. 22, 2005

(87) PCT Pub. No.: WO2004/058667

PCT Pub. Date: Jul. 15, 2004

(65) Prior Publication Data
US 2006/0183926 A1   Aug. 17, 2006

(30) Foreign Application Priority Data
Dec. 24, 2002 (JP) .............................. 2002-371731
Jul. 16, 2003 (JP) .............................. 2003-197750

(51) Int. Cl.
C07C 4/02 (2006.01)
(52) U.S. Cl. .................................................. 585/440
(58) Field of Classification Search ................. 549/512, 549/518; 585/400, 435, 440
See application file for complete search history.

(56) References Cited

U.S. PATENT DOCUMENTS

| 3,127,452 A | | 3/1964 | Codignola | |
|---|---|---|---|---|
| 3,337,646 A | | 8/1967 | Khoobiar | |
| 3,526,674 A | * | 9/1970 | Becker et al. | ............... 585/437 |
| 4,257,877 A | * | 3/1981 | Mahendroo | ............... 208/144 |
| 2003/0032822 A1 | * | 2/2003 | Tsuji et al. | ............... 549/529 |

FOREIGN PATENT DOCUMENTS

| EP | 1266894 A1 | 12/2002 |
|---|---|---|
| GB | 1 269 420 A | 4/1972 |
| GB | 1 555 270 A | 11/1979 |
| JP | 56-140933 A | 11/1981 |
| JP | 2001-270787 A | 10/2001 |
| WO | WO 99/58480 | 11/1999 |

OTHER PUBLICATIONS

*European Chemical News*, Mar. 5-11, 2001, pp. 19-20.
Database WPI Week 198921, Derwent Publications Ltd., London, GB; An 1989-155051 XP002426378.

* cited by examiner

*Primary Examiner*—Karl Puttlitz
(74) *Attorney, Agent, or Firm*—Sughrue Mion Pllc.

(57) ABSTRACT

A process for producing cumene, which comprises supplying cumyl alcohol and hydrogen to a dehydration catalyst to obtain a mixture containing α-methyl styrene and water produced and hydrogen, and supplying the mixture to a hydrogenation catalyst.

6 Claims, No Drawings

PROCESS FOR PRODUCING CUMENE

This application is the National Stage Entry of PCT/JP2003/016074, filed on Dec. 16, 2003, and claims priority to JP 2002-371731, filed on Dec. 24, 2002, and JP 2003-197750, filed on Jul. 16, 2003.

TECHNICAL FIELD

The present invention relates to a process for producing cumene.

BACKGROUND ART

There is publicly known a process for producing cumene by dehydrating cumyl alcohol to convert into α-methyl styrene, subsequently hydrogenating α-methyl styrene in the presence of a hydrogenation catalyst to convert into cumene (for example, European Chemical News, Volume 74, Number 1947, 5-11, March 2001). However, the publicly known process was not necessarily satisfied from the viewpoint of efficient production of cumene at low cost.

DISCLOSURE OF THE INVENTION

The present invention is to provide a process for efficiently producing cumene at low cost.

That is, the present invention relates to a process for producing cumene, which comprises supplying cumyl alcohol and hydrogen to a dehydration catalyst to obtain a mixture containing α-methyl styrene and water produced and hydrogen, and supplying the mixture to a hydrogenation catalyst.

MODE FOR CARRYING OUT THE INVENTION

In the present invention, when cumyl alcohol is dehydrated in the presence of a dehydration catalyst to convert into α-methyl styrene and water, it is essential to supply cumyl alcohol and hydrogen to the dehydration catalyst.

The dehydration catalyst includes acids such as sulfuric acid, phosphoric acid and p-toluene sulfonic acid and metal oxides such as activated alumina, titania, zirconia, silica-alumina and zeolites, solid catalysts are preferable from the viewpoint of separation from the reaction mixture, and further activated alumina is preferable from the viewpoint of catalyst life, selectivity, etc.

The dehydration is usually conducted by contacting cumyl alcohol with the dehydration catalyst, but, in the present invention, hydrogen is also supplied to the dehydration catalyst to conduct hydrogenation subsequent to the dehydration.

The dehydration can be conducted in a gas phase or liquid phase, further, in the presence or absence of a solvent, and it is preferably conducted in a liquid phase using a solvent. The solvent should be substantially inert to the reactants and products. The solvent may be a substance present in a cumyl alcohol solution to be used. For example, when cumyl alcohol is a mixture with cumene as a product, it is possible to use cumene as a substitute without adding a solvent in particular. As other useful solvents, there can be listed alkanes (e.g. octane, decane, dodecane), mono-cyclic aromatic compound (e.g. benzene, ethylbenzene, toluene) and the like. The dehydration temperature is usually 50 to 450° C., preferably 150 to 300° C. In usual, the pressure is advantageously 10 to 10,000 kPa. The dehydration can be advantageously conducted by using a catalyst in a slurry form or fixed-bed form. In the present invention, α-methyl styrene and water obtained in the hydration are supplied into a hydrogenation catalyst to convert α-methyl styrene into cumene.

As the hydrogenation catalyst, a solid catalyst containing a metal of Group 10 or 11 of the Periodic Table of the Elements, can be listed. Specifically, nickel, palladium, platinum and copper are listed, and palladium and copper are preferable from viewpoint of high yield and suppression of hydrogenation of an aromatic ring. Copper-based catalysts include copper, Raney copper, copper-chromium, copper-zinc, copper-chromium-zinc, copper-silica, copper-alumina and the like. Palladium-based catalysts include palladium-alumina, palladium-silica, palladium-carbon and the like.

Though the hydrogenation is carried out by contacting α-methyl styrene and hydrogen with the hydrogenation catalyst, water in a mixture obtained by the dehydration is supplied together with α-methyl styrene and hydrogen to the hydrogenation catalyst for carrying out the hydrogenation subsequent to the dehydration. The hydrogenation can be conducted in a liquid or gas phase in the presence or absence of a solvent, but it is preferable to use the solvent. The solvent should be substantially inert to the reactants and products. The solvent may be a substance existing in an α-methyl styrene solution to be used. For example, when α-methyl styrene is a mixture with cumene as a product, it is possible to use cumene as a substitute of the solvent without adding a solvent in particular. As other useful solvents, there can be listed alkanes (e.g. octane, decane, dodecane), mono-cyclic aromatic compounds (e.g. benzene, ethylbenzene, toluene) and the like. The hydrogenation temperature is usually 0 to 500° C., preferably 30 to 400° C. In usual, the pressure is advantageously 100 to 10,000 kPa.

The feature of the present invention is to produce cumene by supplying cumyl alcohol and hydrogen to the dehydration catalyst, and then supplying the mixture containing α-methyl styrene and water produced and hydrogen to the hydrogenation catalyst.

Preferable embodiments thereof are as follows:

The present invention can be advantageously conducted by a liquid phase continuous method using a catalyst in the form of a fixed-bed. As a reactor used in the continuous method, there are an adiabatic reactor and an isothermal reactor, and the adiabatic reactor is preferable because the isothermal reactor requires an apparatus for removal of heat. In a case of the adiabatic reactor, the temperature lowers with progress of the reaction because the dehydration of cumyl alcohol is an endothermic reaction, and on the other hand, since the hydrogenation of α-methyl styrene is an exothermic reaction, the temperature rises with progress of the reaction. As the result, the outlet temperature becomes higher than the inlet temperature because the generated heat quantity is larger.

The reaction temperature and pressure are selected so that water contained in an α-methyl styrene solution after the dehydration, is not condensed. The reaction temperature is preferably 150 to 300° C., and the reaction pressure is preferably 100 to 2000 kPa. When the reaction temperature is lower than 150° C. and the reaction pressure is higher than 2000 kPa, water may be condensed at the outlet of the dehydration, leading to deterioration of the performance of the dehydration catalyst. Further, when the pressure is too high, it is also disadvantageous in the reaction equilibrium of dehydration. When the temperature is higher than 300° C. and the pressure is lower than 100 kPa, it may become disadvantageous because the gas phase part much generates and the lowering of the catalyst life is accelerated by howling and the like.

Hydrogen can be supplied from the inlet of the fixed-bed reactor, namely the inlet of the dehydration catalyst, or, in addition thereto, from the inlet of the hydrogenation catalyst, and it is preferable to supply from only the inlet of the fixed-bed reactor in view of the activity of the dehydration catalyst and complication of equipments. That is, vaporization of water produced through dehydration is promoted by bringing into anytime existence of hydrogen in the dehydration zone and the equilibrium dehydration conversion rises, therefore, high conversion can be attained effectively compared to absence of hydrogen.

Though water generated in the dehydration is passed through the hydrogenation catalyst, it is possible to operate at low cost without particularly setting up an apparatus for water removal as described above, by operating at the level not condensing water.

The amount of the dehydration catalyst may be an amount of which cumyl alcohol is sufficiently converted, and the conversion of cumyl alcohol is preferably 90% or more.

The amount of the hydrogenation catalyst may be an amount of which α-methyl styrene is sufficiently converted, and the conversion of α-methyl styrene is preferably 98% or more. From the viewpoint of cost, it is preferable that the dehydration catalyst and hydrogenation catalyst are packed in single fixed-bed reactor without using multi stage reactors.

The inside of the reactor may be divided into several beds or not. When the inside is not divided, the dehydration catalyst and hydrogenation catalyst may be directly contacted each other, or may be partitioned with inert packing.

The process of the present invention is preferably applied to a dehydration step and hydrogenation step of the production process of propylene oxide. That is, among steps described below, dehydration of cumyl alcohol and hydrogenation of α-methyl styrene obtained by the dehydration, can be conducted by the above-described methods:

oxidation step: a step of obtaining cumene hydroperoxide by oxidizing cumene;

epoxidation step: a step of obtaining propylene oxide and cumyl alcohol by reacting cumene hydroperoxide contained in a cumene solution with propylene in an excess amount in the presence of an epoxidation catalyst in a liquid phase;

dehydration step: a step of obtaining α-methyl styrene by dehydrating cumyl alcohol obtained in the epoxidation step in the presence of a dehydration catalyst; and hydrogenation step: a step of converting α-methyl styrene into cumene in the presence of a hydrogenation catalyst and recycling cumene to the oxidation step as a raw material.

The oxidation step is a step for obtaining cumene hydroperoxide by oxidizing cumene. The oxidation of cumene is usually conducted by auto-oxidation using an oxygen-containing gas such as air or oxygen-concentrated air. This oxidation may be conducted without use of an additive, and an additive such as an alkali may be used.

The reaction temperature is usually from 50 to 200° C., and the reaction pressure is usually between atmospheric pressure and 5 MPa. In the oxidation method in which the additive is used, an alkali metal compound such as NaOH or KOH, an alkaline earth metal compound, or alkali metal carbonate such as $Na_2CO_3$ or $NaHCO_3$, ammonia, $(NH_4)_2CO_3$, an alkali metal ammonium carbonate or the like, is used as the alkali reagent.

The epoxidation step is a step for obtaining propylene oxide and cumyl alcohol by reacting cumene hydroperoxide obtained in the oxidation step with propylene in an excess amount in the presence of an epoxidation catalyst in a liquid phase.

As the catalyst, solid catalysts are preferable from the viewpoint of separation of reaction products, and catalysts containing titanium-containing silicon oxide, are preferable from the viewpoint of obtaining the objective product under high yield and high selectivity. As these catalysts, so-called Ti-silica catalysts containing Ti chemically bonded to silicon oxide, are preferable. For example, a catalyst prepared by supporting a Ti compound on a silica carrier, a catalyst prepared by combining a Ti compound with silicon oxide by a coprecipitation method or sol gel method, zeolite compounds containing Ti, and the like, can be listed.

Cumene hydroperoxide used as the raw material in the epoxidation step, may be a dilute or dense purified material or non-purified material.

The epoxidation is conducted by contacting propylene and cumene hydroperoxide with the catalyst. The reaction is carried out in a liquid phase using a solvent. The solvent should be liquid under temperature and pressure in the reaction, and substantially inert to reactants and products. The solvent may be a substance present in a hydroperoxide solution to be used. For example, when cumene hydroperoxide is a mixture with cumene which is a raw material thereof, the cumene can be used as a substitute of a solvent without particularly adding a solvent. Additionally, monocyclic aromatic compounds (e.g. benzene, toluene, chlorobenzene, orthodichlorobenzene), alkanes (e.g. octane, decane, dodecane) and the like, can be listed as useful solvents.

The epoxidation temperature is usually from 0 to 200° C., and preferably from 25 to 200° C. The pressure may be a pressure sufficient to keep the reaction mixture in a liquid condition. In general, the pressure is advantageously from 100 to 10000 kPa.

The solid catalyst can be advantageously used in the form of a slurry or fixed bed. In the case of a large-scale industrial operation, a fixed bed is preferably used. In addition, the epoxidation can be conducted by a batch-wise method, a semi-continuous method or a continuous method.

The molar ratio of propylene to cumene hydroperoxide supplied to the epoxidation step, is preferably 2/1 to 50/1. When the ratio is smaller than 2/1, the efficiency may be deteriorated by lowering of a reaction rate, on the other hand, when the ratio is larger than 50/1, large energy in the recycling may be required because the amount of propylene to be cycled becomes bigger. The dehydration and hydrogenation steps are steps for obtaining α-methyl styrene by dehydrating cumyl alcohol obtained in the epoxidation step and subsequently obtaining cumene by hydrogenating it and recycling the cumene as a raw material to the oxidation step, respectively, as described above.

EXAMPLE

Next, the present invention is explained by Examples.

Example 1

A cumene solution containing 25% by weight of cumyl alcohol and hydrogen were passed upwardly through a single reactor, in which activated alumina as a dehydration catalyst and 60 wt % copper/silica as a hydrogenation catalyst were packed in this order, from the dehydration catalyst side. At this time, the pressure was 1 MpaG, the temperature was 205° C. at the inlet of the reactor, hydrogen of 1.5 times by mole of cumyl alcohol was used and the gas linear velocity was 14 cm/sec (converted under the normal temperature and pressure). The conversion of cumyl alcohol at the outlet of activated alumina was 99%, the conversion of α-methyl styrene at the outlet of the copper/silica was 99% and the overall selectivity of cumene was 99%.

Example 2

It was carried out in the same manner as in Example 1 except that the pressure was changed to 1.4 MPaG and hydrogen was used 2.0 times by mole of cumyl alcohol. The conversion of cumyl alcohol at the outlet of activated alumina was 99%, the conversion of α-methyl styrene at the outlet of the copper/silica was 99% and the overall selectivity of cumene was 99%.

Example 3

A cumene solution containing 25% by weight of cumyl alcohol and hydrogen were passed upwardly through a single reactor in which activated alumina as a dehydration catalyst and 0.05 wt % palladium/alumina as a hydrogenation catalyst were packed in this order, from the dehydration side. At this time, the pressure was 1.4 MPaG, the temperature was 205° C. at the inlet of the reactor, hydrogen of 1.5 times by mole of cumyl alcohol was used and the gas linear velocity was 14 cm/sec (converted under the normal temperature and pressure). The conversion of cumyl alcohol at the outlet of activated alumina was 99%, the conversion of α-methyl styrene at the outlet of the palladium/alumina was 99% and the overall selectivity of cumene was 99%.

INDUSTRIAL APPLICABILITY

As described above, according to the present invention, there can be provided a process for producing effectively cumene at low cost.

The invention claimed is:

1. A process for producing cumene, which comprises supplying cumyl alcohol and hydrogen to a dehydration catalyst to obtain a mixture containing α-methyl styrene and water produced and hydrogen, and supplying the mixture to a hydrogenation catalyst.

2. The process according to claim 1, wherein the dehydration catalyst is activated alumina.

3. The process according to claim 1, wherein the hydrogenation catalyst is a catalyst containing a metal of Group 10 or 11 of the Periodic Table.

4. The process according to claim 3, wherein the metal is palladium or copper.

5. The process according to claim 1, wherein the dehydration catalyst and the hydrogenation catalyst are packed in a single fixed-bed flow reactor.

6. A process for producing propylene oxide, which comprises the following steps:

oxidation step: a step of obtaining cumene hydroperoxide by oxidizing cumene;

epoxidation step: a step of obtaining propylene oxide and cumyl alcohol by reacting cumene hydroperoxide contained in a cumene solution with propylene in an excess amount in the presence of a epoxidation catalyst in a liquid phase;

dehydration step: a step of obtaining α-methyl styrene by dehydrating cumyl alcohol obtained in the epoxidation step in the presence of a dehydration catalyst; and hydrogenation step: a step of hydrogenating a-methyl styrene in the presence of a hydrogenation catalyst to convert into cumene;

and recycling it to the oxidation step as a raw material, wherein said dehydrogenation step and said hydrogenation step are carried out by a method according to any one of claims 1 to 5.

* * * * *